United States Patent [19]
Taylor

[11] 3,934,021
[45] Jan. 20, 1976

[54] PREVENTION OF APPLE SCALD
[75] Inventor: Alan Stokoe Taylor, Croydon, Australia
[73] Assignee: ICI Australia Limited, Melbourne, Australia
[22] Filed: Apr. 1, 1975
[21] Appl. No.: 564,209

[30] Foreign Application Priority Data
Apr. 22, 1974  Australia............................. 7323/74

[52] U.S. Cl................ 424/341; 426/310; 426/615; 426/321; 424/340; 426/268; 426/270
[51] Int. Cl.²....................... A23F 1/06; C01B 33/08
[58] Field of Search.......... 426/321, 323, 326, 335, 426/532, 615, 654, 310, 506, 268, 270; 424/346, 341, 340

[56] References Cited
UNITED STATES PATENTS

| | | | |
|---|---|---|---|
| 2,450,615 | 10/1948 | Schomer | 426/323 |
| 2,572,855 | 10/1951 | Guy | 424/346 |
| 2,666,708 | 1/1954 | Chenicek | 426/321 |
| 2,809,914 | 10/1957 | Stokstad | 424/346 |
| 3,526,520 | 9/1970 | Kleiman | 426/321 |
| 3,784,699 | 1/1974 | Yamano | 426/335 |

FOREIGN PATENTS OR APPLICATIONS

| | | | |
|---|---|---|---|
| 2,095,616 | 1/1972 | France | 426/321 |

*Primary Examiner*—Norman Yudkoff
*Assistant Examiner*—Hiram H. Bernstein
*Attorney, Agent, or Firm*—Cushman, Darby & Cushman

[57] ABSTRACT

A method for preventing or inhibiting scald on apples which method comprises applying to said apples an effective amount of a composition comprising as active ingredient a compound selected from the group consisting of the compounds of the formula (I),

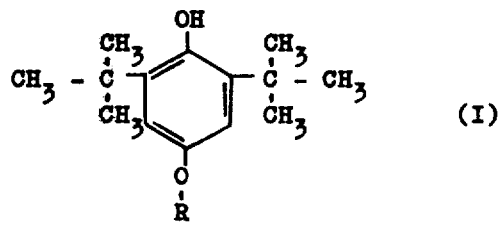

wherein R is methyl or ethyl, and salts thereof; and an inert carrier material therefore.

7 Claims, No Drawings

PREVENTION OF APPLE SCALD

This invention relates to the treatment of fruit, and in particular relates to a method of preventing or inhibiting the occurrence of scald on apples.

Scald is a disease of considerable importance to the apple growing industry in many parts of the world, and in the past has caused significant economic losses. The disease occurs during storage and transportation of the fruit and is characterized by skin discolouration and internal changes which disfigure the apples, shorten the duration of their storage period, and reduce their market value.

We have now found that scald on apples may be prevented or inhibited by application to the fruit of a composition comprising as active ingredient a compound selected from the group consisting of the compounds of formula (I)

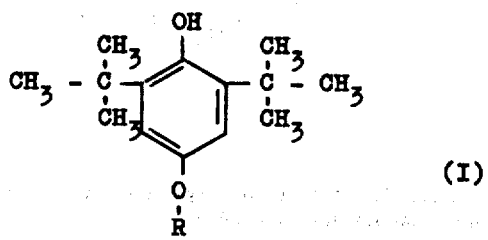

(I)

wherein R is methyl or ethyl, and salts thereof; and an inert carrier material therefore.

Accordingly we provide a method for preventing or inhibiting scald on apples which method comprises applying to said apples an effective amount of a composition comprising as active ingredient a compound selected from the group consisting of the compounds of the formula (I),

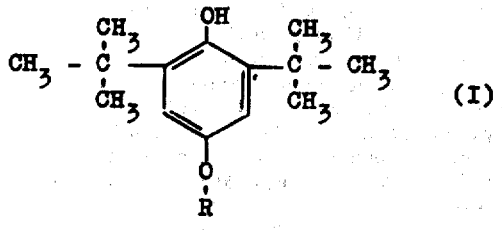

(I)

wherein R is methyl or ethyl, and salts thereof; and an inert carrier material therefore.

Preferably the compositions used to practise the method of the present invention are applied to the apples after picking, and more preferably are applied to the apples within 24 hours of removal from the tree.

The compositions described hereinabove for use in the present invention may be formulated in a number of ways. Aqueous suspensions, solutions or emulsions are generally convenient. These aqueous formulations may be prepared by dissolving or suspending a compound selected from the group consisting of the compounds of formula (I) described hereinabove, and salts thereof, in a liquid inert carrier; suitable liquid inert carriers are solvents which are non-toxic and which do not damage the fruit itself. These compositions may comprise in addition one or more wetting, dispersing or emulsifying agents. Such compositions are then diluted with water which may likewise contain one or more wetting, dispersing, or emulsifying agents, to provide a desired active ingredient compound concentration. Suitable organic solvents are for example propylene glycol, methanol, ethanol, and acetone.

Aqueous formulations for use in the method of the present invention may also be prepared by dilution of suitable wettable powders or cols comprising an active ingredient compound selected from the group of compounds described hereinabove.

When aqueous compositions as described above are utilized in the method of the present invention they are preferably applied to the apples by spraying or dipping. More preferably the said compositions are applied to the said apples by means of a dipping process.

Compositions for use in the method according to the present invention may also be formulated as powders or dusts by admixing an active ingredient compound selected from the group described hereinabove with a solid inert carrier.

Suitable solid inert carriers may be, for example, kaolin, powdered chalk, talcs, kieselguhr, dolomite, calcium carbonate, powdered magnesia, Fuller's earth, gypsum Hewitt's earth, diatomaceous earth, china clay, bentonite, and other colloidal clays. Formulations of this type may be applied to apples by brushing, for example, during grading of the apples.

In addition compositions for use in the method of the present invention may be formulated by including a desired quantity of an active ingredient compound selected from the group described hereinabove in a suitable wax, and applying the formulation to apples by spraying.

Compositions for use in the method of the present invention may also be formulated by impregnating paper or oil paper with an active ingredient compound selected from the group described hereinabove, and the said compositions may be applied by wrapping apples in the said impregnated paper or oil paper.

The concentration of active ingredient compound in the compositions employed in the method of the present invention is not narrowly critical, but should be at a level which allows ready application of an effective amount of the active ingredient compound to the apples. Thus for example we have found that an effective amount of active ingredient may be applied to apples by dipping in a bath containing from 0.01% w/w to 0.5% w/w, based on the total weight of the bath composition, of 2,6-di-tertiary-butyl-4-methoxy-phenol in suspension, and a small quantity of a suitable wetting agent.

The compositions for use in the method of the present invention may also comprise other biologically active materials such as additional anti-scald agents or fungicides.

EXAMPLE 1

Granny Smith apples were picked in the last week of April 1974. The fruit was hand sorted into a size range of 70 cm to 76 cm diameter and units of 10 fruit were packed in open mesh plastic net bags.

Aqueous suspensions of 2,6-di-(tertiary-butyl)-4-methoxy-phenol having the active ingredient concentrations shown in Table I were prepared. A 250 millilitre volume of each of these suspensions was poured over units of fruit. This procedure was repeated several times so that each unit of fruit was treated a number of times with quarter litre volumes of aqueous suspension having the same active ingredient concentration thus ensuring that all fruit surfaces were thoroughly wetted. The fruit units were then allowed to dry for 2 hours at ambient temperature and were then placed in a small plastic tent. The tent was flushed with nitrogen gas to reduce the oxygen content of the atmosphere therein to two percent, and the carbon dioxide content of the tent atmosphere was reduced with lime scrubbers. The fruit was then stored in this manner and at 0°C for 5½ months.

At the end of this period the fruit units were removed from the tent and given a simulated marketing treatment at 20°C for 7 days before being examined for superficial scald, core flush, skin colour and flavour. The results are presented in Table 1 below.

For the purpose of comparison a fruit unit was treated and stored in substantially the manner described above except that the 250 ml volumes of aqueous 2-6-di-tertiary-butyl-4-methoxy-phenol were replaced with 250 ml volumes of water. The result of this test is also shown in Table 1 below.

TABLE 1

| Concentration of 2,6-di-t-butyl-4-methoxy-phenol in aqueous suspension (ppm) | Superficial Scald % | Core Flush* % | Colour Score** (1-5) | Flavour Score*** (1-10) |
|---|---|---|---|---|
| 300 | 20 | 0 | 2 | 8 |
| 1000 | 0 | 0 | 2 | 8 |
| 3000 | 0 | 0 | 2 | 8 |
| 0(water dip) | 80 | 0 | 2 | 8 |

*Darkening of flesh around core of fruit. Generally an indication of fruit senescence and often associated with superficial scald.
**1 = light coloured skin
5 = dark coloured skin
***1 = poor flavour
10 = excellent flavour

EXAMPLE 3

The procedure of Example 1 was substantially repeated except that after treatment with the aqueous 2,6-di-tertiary-butyl-4-methoxy-phenol suspensions and drying the fruit units were placed in unsealed plastic bags open to the atmosphere and stored in this manner for 5½ months at 0°C.

The results are shown in Table II below.

TABLE II

| Concentration of 2-6-di-tertiary-butyl-4-methoxy-phenol (ppm) | Superficial Scald % | Core* Flush % | Colour* Score (1-5) | Flavour* Score (1-10) |
|---|---|---|---|---|
| 300 | 20 | 0 | 2 | 7 |
| 3000 | 30 | 10 | 2 | 7 |
| 0(water dip) | 90 | 10 | 2 | 7 |

*As for Example 1.

I claim:

1. A method for preventing or inhibiting scald on apples which method comprises applying to said apples an effective amount of a composition comprising as active ingredient a compound selected from the group consisting of the compounds of the formula

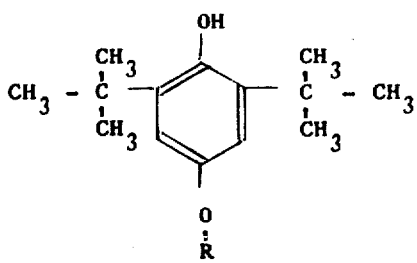

wherein R is methyl or ethyl, and salts thereof; and an inert carrier material therefore.

2. A method according to claim 1 and wherein the said composition is applied to the said apples after picking.

3. A method according to claim 1 and wherein the said composition is applied to the said apples within 24 hours after picking.

4. A method according to claim 1 and wherein the said composition comprises from 0.01% w/w to 0.5% w/w of said active ingredient compound.

5. A method according to claim 1 and wherein the said inert carrier material is water.

6. A method according to claim 5 wherein the surface of the apples is substantially completely wetted with the said composition.

7. A method according to claim 1 which method comprises dipping said apples into an aqueous dispersion or suspension of the said active ingredient compound, of formula (1) as described hereinabove, which aqueous dispersion or suspension comprises from 0.01% w/w to 1% w/w of said active ingredient compound.

* * * * *